United States Patent [19]

Bell et al.

[11] Patent Number: 4,835,102

[45] Date of Patent: May 30, 1989

[54] TISSUE EQUIVALENT TEST SYSTEMS

[76] Inventors: Eugene Bell, 1150 High St., Dedham, Mass. 02026; Crispin Weinberg, 6 Stedman St., Brookline, Mass. 02146

[21] Appl. No.: 32,848

[22] Filed: Mar. 31, 1987

[51] Int. Cl.$^4$ .................. C12Q 1/02; A01N 1/02; A01N 63/02

[52] U.S. Cl. .................................. 435/29; 435/1; 435/283; 435/284; 435/289; 424/95

[58] Field of Search ............... 435/29, 1, 283, 284, 435/289; 424/95

[56] References Cited

U.S. PATENT DOCUMENTS

| | | | |
|---|---|---|---|
| 4,485,096 | 11/1984 | Bell | 424/95 |
| 4,485,097 | 11/1984 | Bell | 424/95 |
| 4,539,716 | 9/1985 | Bell | 623/1 |
| 4,546,500 | 10/1985 | Bell | 623/1 |
| 4,559,299 | 12/1985 | Rotman | 435/284 |
| 4,604,346 | 10/1984 | Bell et al. | 435/1 |
| 4,629,686 | 12/1986 | Gruenberg | 435/1 |

OTHER PUBLICATIONS

*J. Pharm. Sci.*, vol. 74, No. 1, Jan. 1985, Bronaugh & Stewart, Methods for In Vitro Percutaneous Absorption Studies IV: The Flow-Through Diffusion Cell, pp. 64–67.

*J. Invest. Dermatol.*, vol., Mar. 1975, Thomas J. Franz, Percutaneous Absorption, on the Relevance of in vitro, pp. 190–195.

*Science*, vol. 211, Mar. 6, 1981, Eugene Bell et al., Living Tissue Formed in vitro and Accepted as Skin Equivalent Tissue of Full Thickness, pp. 1052–1054.

*J. Invest. Dermatol.*, vol. 81, No. 1 Supplement, July 1983, Eugene Bell et al., The Reconstruction of Living Skin, pp. 2s–10s.

*Collagen Rel. Res.*, vol. 4, 1984, Betty Nusgens et al., Collagen Biosynthesis by Cells in a Tissue Equivalent Matrix In Vitro, pp. 351–364.

*J. Invest. Dermatol.*, vol. 82, No. 4, Apr. 1984, Bernard Coulomb et al., The Contractility of Fibroblasts in a Collagen Lattice is Reduced by Corticosteroids, pp. 341–344.

*Science*, vol. 230, Nov. 1985, P. Saiag et al., Psoriatic Fibroblasts Induce Hyperproliferation of Normal Keratinocytes in a Skin Equivalent Model in Vitro, pp. 669–672.

*J. Invest. Dermatol.*, vol. 87, No. 5, Nov. 1986 B. Topol et al., Transfer of Melanosomes in a Skin Equivalent Model in Vitro, pp. 642–647.

*Science*, vol. 231, Jan. 24, 1986, Crispin B. Weinberg and Eugene Bell, A Blood Vessel Mode Constructed from Collagen and Cultured Vascular Cells, pp. 397–400.

Organogenesis, Inc. Prospectus, Dec. 11, 1986; Supplemental Feb. 4, 1987.

*J. of Dermatol.*, (1986) 114,91–101 B. Coulomb et al., A New Method for Studying Epidermalization In Vitro.

*Scanning Electron Microscopy*, vol. IV (1984) (pp. 1957–1962) Bell et al., The Living Skin-Equivalent as a Structural and Immunological Model in Skin Grafting.

*J. Invest. Dermatol.*, vol. 81(1983)75–78, B. Coulomb et al., Endogenous Peroxidases in Normal Human Dermis: A Marker of Fibroblast Differentiation.

*Mechanisms of Ageing and Development*, 17(1981)107–117, R. Sarber et al., Regulation of Proliferation of Fibroblasts of Low and High Population Doubling Levels Grown in Collagen Lattices.

Organogenesis, Inc.—1986 Annual Report.

Securities and Exchange Commission, Form 10-K Report for fiscal year ended Dec. 31, 1986.

*Primary Examiner*—Robert J. Warden
*Assistant Examiner*—Janelle Graeter
*Attorney, Agent, or Firm*—David G. Conlin; Linda M. Buckley

[57] ABSTRACT

The present invention provides methods of, apparatus for, and kits for determining the interaction of tissue and at least one agent by use of at least one tissue equivalent. Tissue equivalent includes, but is not limited to, equivalents of epithelial tissue, connective tissue, cartilage, bone, blood, organs, glands and blood vessels, which are composed of living cells and extracellular matrix molecules, principally collagen. Agent includes, but is not limited to, various substances such as chemicals, cosmetics, pharmaceuticals, stimuli, e.g., light or physical injury; and tissue protective agents.

54 Claims, 2 Drawing Sheets

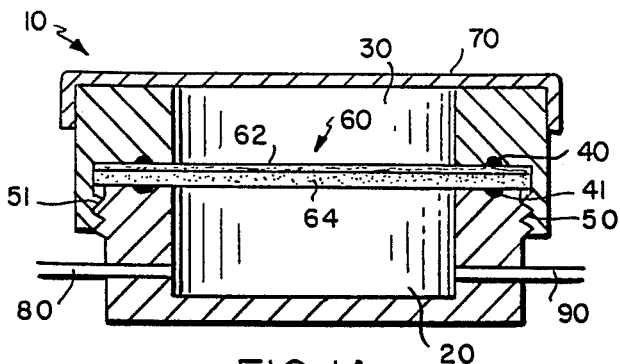
FIG. IA
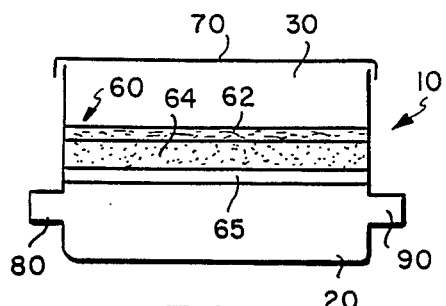
FIG. IB
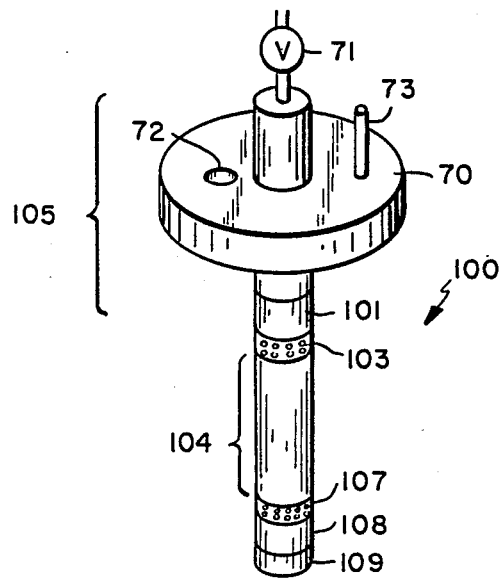
FIG. 3
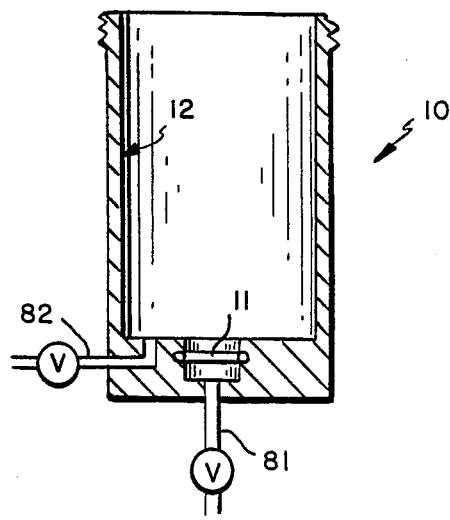
FIG. 2
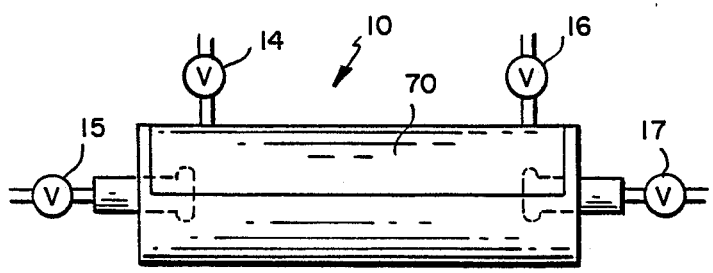
FIG. 4A
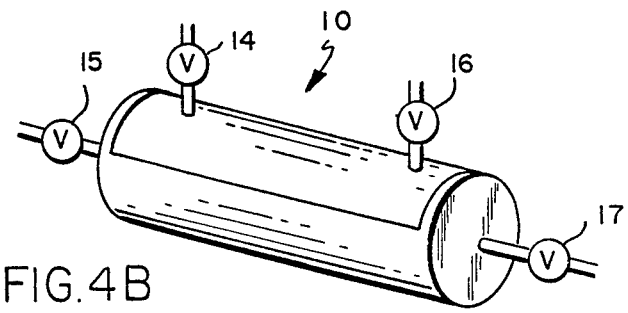
FIG. 4B

TISSUE EQUIVALENT TEST SYSTEMS

BACKGROUND OF THE INVENTION

Many tests have been devised to determine the interaction of various agents and tissues of humans and animals.

Tissue as used herein comprises any group or layer of cells which together perform one or more certain functions. Tissue includes, but is not limited to, epithelial tissue, connective tissue, cartilage, bone, blood, organs, glands and blood vessels.

The effects of chemicals found in the environment, both on man and animals, is of widespread concern. The effects of new drugs, both veterinarian and human, are routinely tested in accordance with federal regulations. Chemical companies, petroleum and paint companies pharmaceutical companies, and cosmetic companies use test systems to assay the reaction of skin to the substances they use and produce. In addition, biomedical laboratories in pharmaceutical companies, hospitals, and universities use test systems for the study of disease mechanisms and for the evaluation of treatment procedures.

At present, systems for determining the interaction of tissues and agents include (i) experimental animals (mainly rodents and rabbits), (ii) monolayer cultures of human cells, (iii) tissue slices or organs from cadavers, and (iv) mathematical models developed to simulate biological responses. Each of these test systems has its advantages and its shortcomings.

Experimental animals (excluding human subjects) have been widely used. Because the cells and tissues of these animals are different from those of humans the use of experimental animals to determine the effect of various agents on man is limited. Furthermore, experimental animals are expensive to maintain, and there are ethical considerations associated with the use of animals for such purposes.

Cultures of cells are highly reproducible, inexpensive, well standardized test systems, but they do not mimic the state of cells and tissues in the organism. As a consequence, the biosynthetic activities and physiologic functions expressed by cells grown in monolayer cultures are markedly different from those in the organism, thus yielding misleading test findings.

Tissue slices from cadavers can provide both the complexity as well as the normal biosynthetic output and cell properties needed for a test system capable of mimicking human responses; however, they are moribund. Some cells are alive, others are dying, and many are already dead. This limits their usefulness since, for example, in a toxicity assay, it may be difficult to distinguish between the effects of the test substance and the natural degenerative changes occurring in the cadaver.

Mathematical models are useful when responses are well understood and predictable and when the full range of variables is defined but they are not appropriate for testing new substances.

From the point of view of human health protection, the ultimate test organism is of course the human; however, human testing is subject to stringent limitations. Animals are widely used in testing because they can be dissected and probed invasively, and because they can be used for substances known to be toxic to humans; however, as mentioned previously their responses do not necessarily reflect human responses.

The skin, a very important tissue, is the principal barrier between the organism's internal milieu and the chemical and physical world without. It is thus subject to the ravages of the environment. It is exposed to agents, such as, chemicals and antigenic substances, in the workplace, in the home, and in the atmosphere generally. Medicaments are applied to the skin both for the treatment of systemic conditions by topical therapy, as well as for the management of wounds and numerous disorders that afflict the skin itself. The skin is treated cosmetically to improve its appearance and sometimes its health. Today there is broad concern with the necessity of establishing safe practices to protect the individual against the effects of intrusive and injurious substances that come into contact with the skin and to evaluate the effects of cosmetic and remedial emollients that are applied to it. Thus, it is not surprising that many tests have been devised to determine the interaction of various substances and human skin.

Skin testing on humans is limited primarily to tests of a "benign" character dealing with sensitization. For example, when human subjects are used to evaluate the effect of test substances on the skin, the skin responses monitored are usually erythema and edema. These are gross manifestations of complex processes that have well defined immunochemical, biochemical, and physiological counterparts at the cellular level. To analyze for such effects requires invasive procedures that are frequently inappropriate.

Although excised cadaver skin has been used for skin testing, it is not readily available and it rapidly becomes moribund. As it degenerates, the skin loses its capacity to respond normally, that is, to emit signals or to metabolize foreign substances. Thus, it becomes impossible to distinguish between effects due to the substance being tested and those due to autolysis and deterioration of the organ in vitro. See, e.g., Bronaugh and Stewart, *J. Pharm. Sci.* 74: 64–67 (1985) and Franz, *J. Invest. Dermatol.*: 190–195 (1975).

The hirsute skin of experimental animals differs fundamentally from the skin of humans in its morphology, its physical properties, and its reactions to allergenic and other stimuli. For example, the rates of percutaneous absorption of animal skin differ considerably from those of human skin. Although, animals will continue to be used to determine LD50 values and the responses to toxic substances of internal organ systems, for many other toxicity studies alternatives to animal testing are being sought, both for ethical reasons as well as for the development of more effective tests (See, e.g., Alternatives to Animal Use in Research, Testing, and Education. Office of Technology Assessment. Washington, D.C. (1985)).

Although cell cultures have many uses as test systems, it has been rigorously shown that the cells grown in monolayer cultures exhibit neither the same biosynthetic repertoire nor the same permeability properties as cells in the organism, nor are they organized or differentiated in the same manner as cells in a tissue or organ.

Thus, alternatives to animal testing and cell culture test systems are being sought. Equivalents of tissue that reproduce in vitro many of the physical and biological characteristics of natural tissues would be useful for the study of the tissue cell biology, physiology and pathology.

SUMMARY OF THE INVENTION

The present invention provides methods of, apparatus for, and kits for determining the interaction of tissue and at least one agent by use of at least one tissue equivalent.

Tissue/agent interactions which may be determined in accordance with the present invention, include but are not limited to, the passage of the agent into or through the tissue equivalent; the production or release of one or more substances by the tissue equivalent; and a change in permeability, proliferation, differentiation, or configuration of cells of the tissue equivalent. In some embodiments the interaction of the tissue and the agent serves to protect the tissue. The agents tested include, but are not limited to, various stimuli, e.g., light, physical injury, and various substances, e.g., chemicals, cosmetics, pharmaceuticals and tissue protective agents.

Various types of tissue equivalents may be used in the practice of the present invention and include, but are not limited to, epithelial, connective, cartilage, bone, organ, gland and blood vessel tissue equivalents. The composition and configuration of the tissue equivalent will be selected in light of the nature of the interaction studied and limitations of the assay procedure used to determine the interaction. A tissue equivalent may be cast in any desired configuration.

One method according to the present invention of determining the interaction of tissue and at least one agent by use of at least one tissue equivalent comprises the steps of:
 a. contacting the agent with a tissue equivalent, wherein the tissue equivalent is adjacent to a liquid phase; and
 b. determining the interaction of the tissue equivalent and the agent by analyzing at least one of (i) the tissue equivalent, (ii) an intracellular fluid of the tissue equivalent, or (iii) the liquid phase.

In other methods provided by the present invention, at least one tubular tissue equivalent is used to determine the interaction of tissue and at least one agent, the method comprising:
 a. contacting the agent with the lumen or abluminal surface of the tubular tissue equivalent, such contact being effected by providing a liquid phase adjacent to the lumen or the abluminal surface of the tubular tissue equivalent, and introducing the agent into the liquid phase; and
 b. determining the interaction of the tubular tissue equivalent and the agent by analyzing at least one of (i) the tubular tissue equivalent, (ii) the intracellular fluid of the tubular tissue equivalent, or (iii) the liquid phase.

Preferred tubular tissue equivalents include skin, blood vessels and glands.

One apparatus according to the present invention for determining the interaction of tissue and at least one agent by use of at least one tissue equivalent, comprises a container for the tissue equivalent, the container comprising:
 (i) means for positioning the tissue equivalent in the container, whereby the tissue equivalent defines at least one region in the container;
 (ii) at least one port; and
 (iii) means for closing the container. When the tissue equivalent is included in apparatus of the present invention, the tissue equivalent is preferably positioned in the container so that it defines at least two regions in the container.

In some embodiments the tissue equivalent defines an upper and a lower region in the container. In yet other embodiments wherein the tissue equivalent is a tubular tissue equivalent, the tubular tissue equivalent is positioned so that it defines an inner and an outer region in the container. In some embodiments, the container is further provided with one or more liquid phases.

Various means for positioning a tissue equivalent in a container are taught by the present invention. In some embodiments of the present invention, the means for positioning a tissue equivalent in the container is disposed in the container and comprises a permeable member.

In yet other embodiments of apparatus according to the present invention, the tissue equivalent is a tubular tissue equivalent, and the means for positioning the tubular tissue equivalent in the container comprises (i) means for attaching the tubular tissue equivalent to the means for positioning the tubular tissue equivalent in the container, (ii) means for limiting the longitudinal contraction of the tubular tissue equivalent, and (iii) means for allowing selected materials to pass between the tubular tissue equivalent and at least one liquid phase. The means for positioning the tissue equivalent may also serve as a support member for the tissue equivalent. Furthermore, in some embodiments, the tissue equivalent may be cast on the means for positioning the tissue equivalent if desired.

The present invention includes methods of determining the interaction of tissue and at least one agent with the aid of an apparatus for determining the interaction of tissue and at least one agent by use of at least one tissue equivalent, the apparatus comprising a container for the tissue equivalent, the container comprising:
 (a) means for positioning the tissue equivalent in the container, whereby the tissue equivalent defines at least one region in the container;
 (b) at least one port; and
 (c) a means for closing the container; and the method comprising the steps of:
 (a) contacting the agent with the tissue equivalent; and
 (b) determining the interaction of the tissue equivalent and the agent by analyzing at least one of (i) the tissue equivalent (ii) an intracellular fluid of the tissue equivalent, or (iii) the liquid phase.

Apparatus of the present invention may be incorporated into kits which comprise, in combination:
 (a) an apparatus for determining the interaction of tissue and at least one agent by use of at least one tissue equivalent, the apparatus comprising a container for the tissue equivalent, the container comprising:
  (i) means for positioning the tissue equivalent in the container, whereby the tissue equivalent defines at least one region in the container; and
  (ii) at least one port; and
 (b) a tissue equivalent.

In preferred embodiments, the tissue equivalent is positioned so that it defines at least two regions. The apparatus of such kits may be further provided with one or more liquid phases. In preferred embodiments of kits of the present invention, the apparatus is provided with two or more individual containers. In other embodiments of kits, the containers are interconnected so that the liquid phase is common to each tissue equivalent.

One or more reagents for use in determining the interaction of the tissue equivalent and the agent are optionally included in the kits of the instant invention.

BRIEF DESCRIPTION OF THE DRAWINGS

FIG. 1A is a cross-section through the center of one apparatus according to the present invention.

FIG. 1B is a diagrammatical view of another apparatus of the present invention.

FIG. 2 is a cross-section through the center of a container according to the present invention.

FIG. 3 is an isometric view of a means for positioning a tubular tissue equivalent together with a cover means both in accordance with the present invention.

FIG. 4A is a side view of another embodiment of an apparatus provided by the present invention.

FIG. 4B is a diagrammatical view of FIG. 4A.

DETAILED DESCRIPTION OF THE INVENTION

Figure 4C:
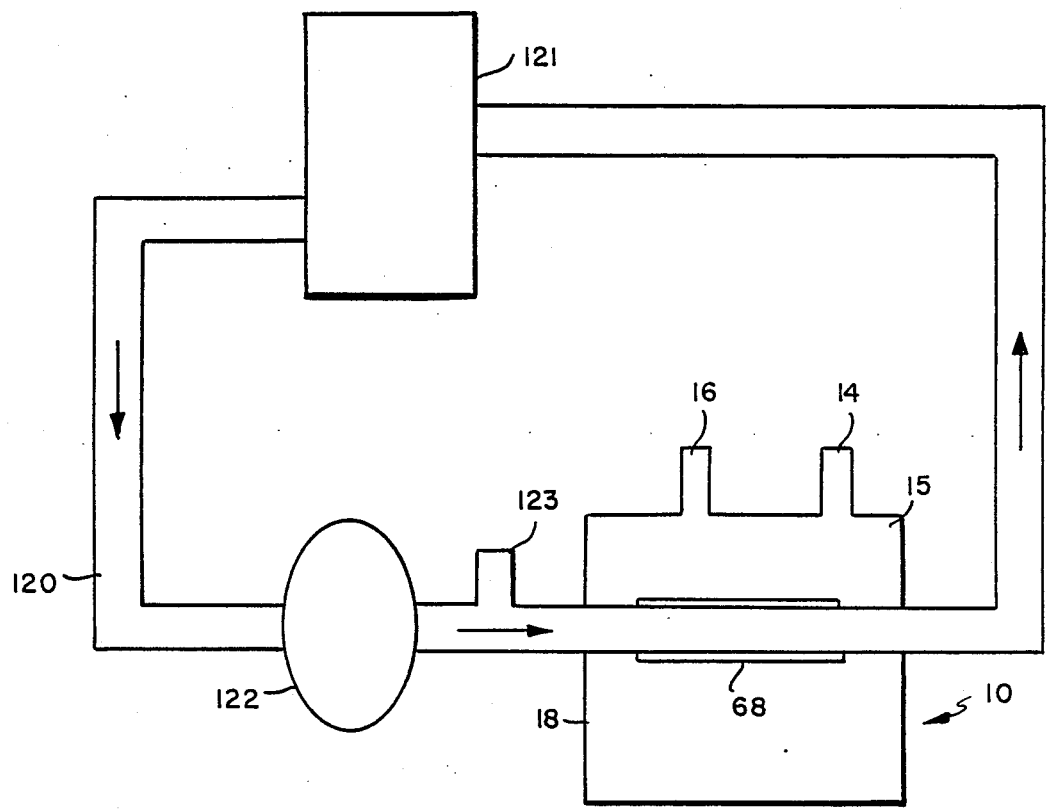
FIG. 4C is a schematic view of one apparatus provided by the present invention, the apparatus being incorporated in a circulatory loop.

The present invention provides apparatus for, methods of, and kits for determining the interaction of tissues and one or more agents by use of tissue equivalents. The apparatus, methods and kits provided by the present invention will be illustrated for human skin tissue equivalents and blood vessel tissue equivalents. However, other tissue equivalents such as gland and bone are equally suitable for use in such methods, apparatus and kits.

As previously mentioned, tissue is used in this application in the usual biological sense, i.e., tissue as used herein comprises any group or layer of cells which together perform one or more certain functions.

Agent as used herein includes, but is not limited to, various substances such as chemicals, cosmetics, pharmaceuticals, stimuli, e.g., light or physical injury, and tissue protective agents.

The tissue/agent interactions determined in accordance with the present invention include the myriad of interactions normal tissues are subject to. These interactions include, but are not limited to, the rate and extent of penetration of agents into or through the tissue, changes in tissue permeability, the release of one or more substances by a tissue into its intracellular tissue fluids, the effect on tissue metabolism or cell proliferation or differentiation, and reorganozation of the cells of the tissue. In some embodiments of the present invention, the interaction determined comprises the effect of the tissue on the agent, e.g. where a tissue breaks down an agent. In other embodiments, the agent is a nutrient or precursor and the interaction is the synthesis or production of a substance. In yet other embodiments, the interaction determined may be the protection conferred on a tissue by one or more agents. In yet other embodiments of the present invention, more than one agent is used to determine the agent/tissue interaction, e.g., the interaction of a tissue and a first agent may be determined by use of a second agent. For example, a tissue equivalent is contacted with a first agent. A second agent is subsequently contacted with the tissue equivalent, and the first agent prevents or reduces the interaction of the second agent and the tissue equivalent.

Tissue equivalent, as used herein, shall include, but is not limited to, epithelial tissue, connective tissue, cartilage, bone, blood, organs, glands and blood vessels comprising living cells and extracellular matrix molecules principally collagen. See, for example, U.S. Pat. Nos. 4,485,096; 4,485,097; 4,539,716; 4,546,500; and 4,604,346; all of which are incorporated herein by reference. Tissue equivalents for use in accordance with the present invention may optionally be provided with components not typically found in normal tissue.

Tissue equivalents for use in the present invention are populated with cells that can remain alive for long periods and can be produced in quantity with the assurance that all units fabricated will be essentially uniform. Such tissue equivalents include, but are not limited to, skin tissue equivalents, organ tissue equivalents, gland tissue equivalents and bone tissue equivalents. Cells in the tissue equivalents used in accordance with the present invention resemble those of normal tissue in their structural arrangement, in their biosynthetic output, and in their permeability. It should be understood that tissue equivalents for use in the present invention need not be human but may be those of any animal as desired.

In some embodiments of the present invention it is desirable to provide tissue equivalents with protective means, e.g., by disposing a removable means for protecting the tissue equivalent on exposed surfaces thereof. A thin, flexible film, e.g., of a plastic, is acceptable for such applications.

Human skin tissue equivalents used in the practice of the present invention permit the growth of normal human epidermal cells that differentiate fully producing a normal stratum corneum and a complete basal lamina which have not, to date, been obtained by routine culture methods. Such skin tissue equivalents have been extensively used as a permanent skin replacement in animal experiments and recently in initial human trials in France; the morphological appearance of such skin tissue equivalent is normal, its constituent cells persist after grafting as shown by genetic marking, and its functional performance has been demonstrated. See, e.g., *Science.* 21: 1052–1054 (1981); *J. Invest. Dermatol.* 81: 2s–10s (1983).

Skin tissue eqivalent fabricated in vitro bears a close resemblance to natural skin. It consists of a multilayered epidermis with well developed basal cells joined to the dermal layer by a fully structured basal lamina. The dermal layer is a collagen matrix in which dermal fibroblasts are distributed. Cells in the three-dimensional collagen matrix achieve a state of differentiation in many respects similar to that which prevails in vivo. For example, fibroblasts are synthetically active and enrich the matrix in vitro with collagen, as well as with a number of other molecular species, and exhibit permeability properties typical of a cell in vivo. See, e.g., *Collagen Rel. Res.* 4: 351–364 (1984). The effects of steroids on the capacity of human and rat fibroblasts to contract tissue equivalent lattices has been evaluated (*J. Invest. Dermatol.* 82: 341–344, 1984). A skin tissue equivalent model has been used to fabricate tissues with psoriatic and normal cells for the study of the disease psoriasis (*Science* 230: 669–672, 1985). Recently it has been shown that skin tissue equivalents can be pigmented by inclusion of melanocytes that donate pigment to keratinocytes and that the process is speeded up in vitro by UV radiation (*J. Invest. Dermatol.* 87: 642–647, 1986).

Human blood vessel tissue equivalents for use in the present invention are multilayered tubes constructed from extracellular matrix molecules and cultured vascular cells. See, e.g., *Science* 231: 397–400, 1986; U.S. Pat. Nos. 4,539,716 and 4,546,500). They resemble human blood vessels in structure and function and are used in the methods, apparatus and kits of the present invention for in vitro and ex vivo bio-tests for the study of normal human vascular physiology and of blood-surface interactions, as well as the study of pathological processes and their amelioration.

In one embodiment of the present invention the blood vessel tissue equivalent is lined with a monolayer of endothelial cells which produce a basal lamina in vitro. Together, the endothelial cells and basal lamina constitute the intima of such blood vessel tissue equivalents. The middle layer consists of smooth muscle cells in a collagen lattice, and constitutes the media of the blood vessel tissue equivalents. The smooth muscle cells contribute collagen, elastin, and other molecules to the matrix. In some embodiments, other extracellular matrix components such as hyaluronic acid are optionally added for particular applications. The outer layer of the blood vessel tissue equivalent is fabricated from adventitial fibroblasts in a collagen lattice and constitutes the adventitia of the blood vessel tissue equivalent. A support member, e.g., a synthetic mesh, may also be optionally included in the blood vessel tissue equivalent, typically in the wall between the media and adventitia, to strengthen the blood vessel tissue equivalent. A removable, protective impermeable member, e.g., a plastic sleeve adjacent the abluminal surface may also be optionally provided.

It should be understood that the order of the layers in the blood vessel tissue equivalents for use in accordance with the present invention may be organized in the reverse order of that typically found in a natural blood vessel. For example, the endothelial cells and basal lamina which constitute the intima of normal blood vessels can be located so that they are on the outside of a tubular blood vessel tissue equivalent. The middle layer of such a blood vessel tissue equivalent consists of smooth muscle cells and a collagen lattice, thereby constituting the media of the blood vessel tissue equivalent. The inner layer of such a reverse order blood vessel tissue equivalent is fabricated from adventitial fibroblasts in a collagen lattice and forms the layer that would constitute the adventitia of a normal blood vessel.

Blood vessel tissue equivalents for use in the present invention can be made for different types of blood vessels by using cells cultured from the appropriate sources. Arterial blood vessel tissue equivalents further comprise cells cultured from the corresponding layers of an artery. Capillary blood vessel equivalents further comprise capillary endothelial cells and pericytes in place of the adventitial fibroblasts. Venous blood vessel tissue equivalents further comprise cells cultured from veins and are fabricated with thinner outer layers than arterial blood vessel tissue equivalents. For the studies of certain diseases in accordance with the present invention, cells cultured from patients with the particular disease are incorporated into the blood vessel tissue equivalent.

The configuration of apparatus according to the present invention will depend upon the tissue equivalent used as well as the nature of the interaction to be determined. Tissue equivalents for use in the present invention are generally cast as a flat sheet, a hollow tube or a network of hollow tubes. However, they can be cast in any desired shape. For example, in some embodiments of the present invention, it is desirable to change the natural geometry of the tissue equivalent. For example, skin tissue equivalent may be cast as a cylinder rather than as a sheet and the layers of blood vessel tissue equivalent may be cast in the reverse of the order of natural blood vessels.

The present invention provides apparatus for determining the interaction of tissue and at least one agent by use of at least one tissue equivalent, the apparatus comprising a container for the tissue equivalent, the container comprising (i) means for positioning the tissue equivalent in the container, whereby the tissue equivalent defines at least one region in the container; (ii) at least one port; and (iii) means for closing the container. In preferred embodiments of the present invention the tissue equivalent defines at least two regions in the container. Some embodiments of the instant invention further comprise cover means for closing the container. In some such embodiments the cover means is removably sealable to the container.

This invention also includes within its scope apparatus further comprising a tissue equivalent. In some embodiments the tissue equivalent defines an upper and lower region in the container, the lower region further comprising a liquid wherein one surface of the tissue equivalent is adjacent to the liquid. In some such embodiments of the present invention, the upper region is further provided with a second liquid phase. The present invention also includes within its scope apparatus further comprising a tubular tissue equivalent, wherein the tubular tissue equivalent defines an inner and outer region in the container, the inner region comprising a first liquid phase and the outer region comprising a second liquid phase.

Referring to the drawings, FIG. 1A illustrates one embodiment of an apparatus according to the present invention for determining the interaction of skin and one or more agents by use of skin tissue equivalents, the apparatus comprising a container 10, the container providing means for positioning the skin tissue equivalent 60, a lower chamber 20 and an upper chamber 30, the chambers being sealably connected by means of an upper gasket means 40, a lower gasket means 41 and connecting means 50, 51. This embodiment is provided with a skin tissue equivalent 60, removably positioned between the lower chamber 20 and the upper chamber 30. The skin tissue equivalent 60 comprises two layers, layer 62 comprising an epidermal layer, layer 64 comprising a dermal layer. In this embodiment the container 10 is provided with cover means 70 which is placed over the upper chamber 30, and the lower chamber is provided with ports 80, 90.

In the embodiment show in FIG. 1A, the container is provided with sealably connected lower and upper chambers 20 and 30 to provide means for postioning the skin tissue equivalent 60 in the container 10. Other means may be used for positioning a tissue equivalent in the container 10 such as positioning the tissue equivalent in the container by means of a permeable support member disposed in the container, wherein the tissue equivalent attaches to or is cast on the permeable support member. One such embodiment of the present invention is shown in FIG. 1B. Elements similar to those in other described embodiments are indicated by the same numeral. This embodiment comprises a container 10 defining a holder for a skin tissue equivalent 60, container 10 having disposed therein a permeable support member 65, the support member 65 providing means for positioning the skin tissue equivalent 60 in the container 10. This embodiment further comprises a skin tissue equivalent 60, further defining a lower chamber 20 and an upper chamber 30. In this embodiment, the container 10 is provided with a cover means for closing the container 70, which is placed over the upper chamber 30, and the lower chamber is provided with ports 80, 90.

FIGS. 2 and 3 show yet another apparatus according to the present invention. Elements similar to those in other described embodiments are indicated by the same numeral. The apparatus comprises a cylindrical container 10 for a tubular tissue equivalent, the container having two ports, 81, 82, at the bottom, a hollow mandrel 100, the upper end of the mandrel being provided with a port 71, the lower end of the mandrel being open, and a cover means 70 for closing the container 10, the cover means being sealably connectable to the mandrel 100. The inner surface 12 of the container 10 comprises an inert, non-wettable material. The container 10 is threaded to accept the cover 70 for removably sealing the container 10. The cover means 70 is provided with a port 72. The port 72 may also serve as a vent during filling or a separate vent 73 may be provided. The container 10 is further provided, at the bottom thereof, with a means (not shown) for sealing the mandrel 100 to the base of the container. In some embodiments, the bottom of the mandrel 100 is provided with an inlet or outlet means which is provided with means for sealing the bottom of the container. The mandrel 100 shown in FIG. 3 comprises a number of regions: region 105 comprising a means for sealably covering the container; regions 101 and 108 comprising means for the cells of the tubular tissue equivalent to adhere to; regions 103 and 107 comprising means for limiting the longitudinal contraction of the tubular tissue equivalent; region 104 comprising a liquid permeable means for allowing selected materials to pass through the tubular tissue equivalent and, in some embodiments for supporting the tissue equivalent; and region 109 comprising means (not shown) for removably sealing the mandrel 100 to the base 11 of the container 10 (e.g., groove for O-ring or screw threads).

The container 10 and cover means 70 may be made of any desired material which does not react with or have an undesirable effect on the components of the assay, including the tissue equivalent. In some embodiments, it is desirable that the container 10 be made so that the tissue equivalent is visible through the container, e.g., through the walls of the container or through a window in the container. Preferred materials for the container include glass, polycarbonate, polystyrene, TEFLON ®, and stainless steel. In yet other embodiments, the inside 12 the container 10 comprises an inert, non-wettable surface such as TEFLON ®, polycarbonate or stainless steel or the inside 12 is coated to make it non-wettable.

The container may be of any shape and volume which will accomodate the size and shape of the desired tissue equivalent. The dimensions of the container will again depend upon the size and shape of the desired tissue equivalent and the desired assay volumes. For example, a container having an outer diameter of about 25 mm and a volume of about 5 ml is useful in practicing the present invention. In some embodiments of the present invention, multiple containers will be provided in a base or holder.

In embodiments wherein a permeable support member 65 is provided for positioning the tissue equivalent 60 in the container 10 the permeable support member 65 preferably comprises a membrane or a mesh. Preferred materials include polypropylene, nylon, and polycarbonate.

The gasket means 40, 41 may be made of any material which is inert to the conditions of the assay and the tissue equivalent being used, as well as provides a good seal between the upper and lower chambers 20, 30. Preferred materials include silicone and TEFLON ®.

In the embodiment shown in FIG. 1, the upper and lower chambers 20, 30 are attached by screw means 50, 51. It will be appreciated by those of ordinary skill in the art that any suitable connecting means may be used to sealably attach the upper and lower chambers.

The apparatus shown in FIGS. 1A and 1B are provided with ports so that a liquid phase may be passed into and out of the lower chamber 20. The desired number of ports for the lower chamber will depend upon the assay being conducted.

In the embodiment shown in FIG. 3, the cover means 70 for the container 10 is provided with a valve 71, a port 72 and a vent 73. In some embodiments, a vent is not provided, and a port 72 may serve both as a port and as a vent. The port may be used, e.g., for epidermalizing the tissue equivalent or applying test agents. It must be understood that although the apparatus shown in the Figures are provided with cover means 70 for closing the container 10, alternative means for closing the container 10 are acceptable. In alternative embodiments, access to the inside of the container or a tissue equivalent positioned therein is achieved by means of ports or other openings or passages appropriately disposed on the container. These openings or passages will be provided with valve means or other means for closure. In yet other embodiments the means for closing the container may be sealed or fused to the container, e.g., as by heat sealing. In such embodiments access to the container is achieved by removing the sealed or fused means for closing the container.

In the embodiment shown in FIGS. 2 and 3, the mandrel 100 provides a means for positioning the tissue equivalent in the container 10. In some embodiments of the present invention, the tissue equivalent is cast on the mandrel 100 after the mandrel 100 has been disposed in the container 10.

As has been described above, the mandrel 100 is comprised of a number of regions. Preferred materials for regions 105 and 109 are rigid, nonporous and inert, and include plastics such as polycarbonate or polystyrene, TEFLON ®, glass or stainless steel or combinations thereof. Regions 101 and 108 comprise means for the cells of the tissue equivalent to adhere to and in some embodiments also provide a seal between the tissue equivalent and the mandrel 100. Preferred materials for regions 101 and 108 include glow discharge treated plastic, collagen or fibronectin-coated glass or plastic. Regions 103 and 107 provide means for limiting the longitudinal contraction of the tissue equivalent. Regions 103 and 107 preferably are highly textured. Texture can be provided, e.g., by providing the region with holes or with numerous fine projections. Preferred materials include, but are not limited to, VELCRO ®, textured stainless steel, e.g., wire cloth, textured plastics, textured TEFLON ® and polyurethane foam. Preferred materials for region 104 include materials which are permeable to small molecules such as nutrients, but are of limited permeability to larger molecules such as collagen and especially to collagen fibrils. Such liquid permeable means include strong but inert materials such as nylon or polypropylene. Pore sizes of about 0.2 to 5 μm are useful; pores of 0.5 to 3 μm are preferred. In some embodiments support means is provided for the membrane. Preferred materials include a framework or a screen of a rigid and inert material, such as stainless steel, plastics including polycarbonate or polystyrene, TEFLON®.

Apparatus according to the present invention may be provided with means for controlling the flow of the liquid phase(s) into and out of the apparatus. Means for controlling the flow of a liquid are well known to those skilled in the art. For example, means for sampling, circulating, exchanging or feeding the liquid phase(s) adjacent to the tissue equivalent may be provided. In the embodiment shown in FIG. 1A, the liquid phase in chamber 20 may be moved through the apparatus by attaching ports 80 and 90 to any appropriate circulatory means known to those skilled in the art.

The present invention provides methods of determining the interaction of tissue with at least one agent by use of at least one tissue equivalent, the method comprising the steps of: (a) contacting the agent with a tissue equivalent, wherein the tissue equivalent is adjacent to a liquid phase; and (b) determining the interaction of the agent with the tissue equivalent by analyzing at least one of (i) the tissue equivalent, (ii) an intracellular fluid of the tissue equivalent, or (iii) the liquid phase.

In some embodiments of the present invention, the interaction of skin and at least one agent is determined by the use of at least one skin tissue equivalent, the skin tissue equivalent having an epidermal and a dermal layer, the method comprising the steps of: (a) contacting the agent with the epidermal layer of the skin tissue equivalent, wherein the dermal layer of the skin tissue equivalent is adjacent to a liquid phase; and (b) determining the effect of the agent on the skin tissue equivalent by analyzing at least one of (i) the skin tissue equivalent, (ii) an intracellular fluid of the skin tissue equivalent, or (iii) the liquid phase.

Apparatus, methods and kits based on human skin tissue equivalent are provided by the present invention for use in determining the interaction of skin and various agents, including, but not limited to, the measurement of:

(1) the rate and extent of penetration of substances into and through the skin (Skin Absorption Test);
(2) the interaction of agents reflected by changes in cell permeability (Skin Cell Permeability Test);
(3) the responses of skin cells to agents that provoke or promote the release of various regulatory or signaling molecules into the intracellular tissue fluids (Skin Chemical Response Test); and
(4) the responses of skin cells together with specialized immune cells to substances that are true allergens (Skin Immunoreactivity Test).

Such apparatus, methods and kits provide means for quantifying the interaction of human skin tissue equivalent to agents. The results of such tests should reflect the response of natural human skin more closely than a corresponding test conducted with animal or cadaver skin.

In some methods according to the present invention, the epidermis is exposed to a gaseous atmosphere, while the dermis is bathed by a sterile tissue culture fluid freely exchangeable with the tissue fluids of the skin tissue equivalent. The skin tissue equivalent is positioned between a gaseous phase (e.g., air) and a fluid phase (e.g., culture medium) (See, e.g., FIG. 1). In such embodiments, the dermal layer of the skin tissue equivalent is adjacent to, typically in contact with, the fluid phase that serves as a nutrient medium simulating the "milieu interieur" while the cornified epidermal layer contacts the gaseous phase simulating the environment. The skin tissue equivalent provides a fluid-tight seal between the two phases; the test substance is applied to its epidermal surface in an appropriate vehicle. The skin tissue equivalent itself, the tissue fluids thereof and the culture medium are each available for analysis.

The composition of skin tissue equivalents for use in tests according to the present invention will vary depending upon the nature of the test to be conducted.

The present invention provides apparatus, methods and kits for use in skin absorption tests which permit a determination of the amount of an agent that traverses the skin during a predetermined period of time. With the exception of the initial phase of absorption, appendageal absorption has generally been found to play a minor role. Thus standard skin tissue equivalents, although lacking appendageal openings such as hair follicles and sweat glands, are expected to be suitable for most steady-state absorption studies. However, in some embodiments of the present invention, it may be desirable to fabricate skin tissue equivalents with a number of cell-lined pores that provide a physiologic ratio of appendageal to non-appendageal percutaneous absorption. Long term testing using skin tissue equivalents is possible because skin tissue equivalents can be maintained in a viable state for many months or even longer.

Skin absorption tests according to the present invention may include measuring the amount of an agent in the liquid phase adjacent to the dermal component of the skin equivalent, or directly in the skin tissue equivalent itself or intracellular fluids thereof since lipid soluble substances, for example, tend to become entrapped in skin. Agents used in such tests are capable of being detected in some way, e.g., labeled with radioactivity, or are measured by direct assay, using methodologies known to those skilled in the art.

Some methods according to the present invention measure the kinetics of skin penetration by the agent(s) under test. In some such embodiments, an apparatus according to the present invention is provided with multiple containers in a holder therefor, mounted into a jig and coupled to a reservoir for feeding each sample skin tissue equivalent periodically or continuously with, e.g., a nutrient solution to bathe the dermis. The pumped or gravity-feed output allows for fraction collecting so that flow through as a function of time under conditions simulating blood flow is measurable. The data is used to calculate the permeability constant or other relevant parameters, such as, the time for initial permeation or the percentage absorbed of the agent. Such methods also provide an optional calibration step that uses tritiated water before and after testing penetration so that the effects of the agent on the barrier properties of the skin tissue equivalent are determined.

The present invention also provides apparatus, methods and kits for use in skin cell permeability tests to determine changes in cell permeability brought about by the interaction of skin and agents such as chemicals, cosmetics or drugs. The release by cells of strictly intracellular proteins may serve as an indicator of cell damage due to the agent under test. Dose response data is derived by testing multiple skin tissue equivalents using apparatus, methods, and kits in accordance with the present invention, each skin tissue equivalent being positioned in an individual container which is provided with its own fluid phase, the contents of which are available for assay. The release of a cytoplasmic protein such as LDH is measured, for example, chromogenically. Release of at least one cytoplasmic and one lysosomal enzyme is measured by use of appropriate assay techniques well known to those skilled in the art. For example, various protein-binding methodologies including radioimmunoassay (RIA), enzyme immunoassay (EIA), enzyme-linked immunoassay (ELISA), and fluorescent immunoassay are useful. The skin cell permeability test of the present invention is especially useful for discriminating between irritant and corrosive agents since, in general, the former are expected to give negative results, and the latter, positive results.

The present invention also provides apparatus, methods and kits for use in skin chemical response tests for the measurement of physiological responses of skin cells to agents that induce edema and erythema or inflammation. The test is designed to quantitate complex tissue reactions resulting from multiple chemical triggers. Chemicals released from cells into the tissue fluids in response to the agent(s) under consideration are assayed. These include, for example, prostaglandin E2, prostacyclin and other signaling factors of arachidonic acid derivation as well as Interleukin I that can amplify the response by stimulating fibroblasts of the dermis to secrete prostacyclin. Multiple skin equivalent samples provide data for dose response curves.

The degree of release is quantitated using techniques known to those skilled in the art. By testing known contact irritants, release of one or more of these mediators is correlated with the classical, though difficult to quantitate, responses of erythema and edema. While the keratinocytes of the skin tissue equivalents for use in methods provided by the present invention are expected to be the principal emitters of prostaglandin E2, in some embodiments capillary endothelial cells are optionally included in the dermis of the skin tissue equivalent to provide a response source for prostacyclin. Although both factors have relatively short half lives, they can be measured by assaying their degradation products using methods known to those skilled in the art.

Apparatus, methods and kits for use in skin immunoreactivity tests are also provided by the present invention to measure responses to various agents which emanate from immune cells incorporated into the skin tissue equivalent, for example, an agent capable of causing contact sensitivity by forming covalent bonds with proteins. The immunogen will often be a complex of self-protein acting as "carrier" and the contact sensitizer acting as hapten.

In some embodiments of skin immunoreactivity tests according to the present invention, the macrophage-like Langerhans cells (LC) of normal skin which process immunogenic complexes for presentation to other immune cells are incorporated in the epidermis of the skin tissue equivalent to provide the basis for the first step in the immune reaction chain involving the skin. Measurement of the migration of activated LC out of the epidermis of the skin tissue equivalent and of the protein-hapten complex are suitable assays of allergenicity. The movement of cells may be followed by immunofluorescence or other methods known to those skilled in the art and may be correlated with allergenicity by using substances of known allergenicity. In other embodiments, macrophages are optionally included in the skin tissue equivalent to provide another source of the assayable lymphokine, IL-1, secreted by the cells in response to substances that initiate humoral immune reactions. In yet other embodiments, subsets of sensitized T cells that will respond to particular classes of immunogens, together with mast cells that release strong signals such as histamine, are optionally incorporated in the skin tissue equivalent to provide immune signals, easily assayed because of their degree of amplification.

Mediators are collected from the culture fluid in contact with the dermis or from the tissues themselves for assay. With the skin irritation test and skin chemical reaction test, the user will be able to discriminate between irritants and allergens.

The apparatus and methods of the present invention may be used in the production of kits for determining the interaction of tissue with at least one agent by use of one or more tissue equivalents. One kit according to the present invention comprises the following in combination:
 (a) an apparatus for determining the interaction of tissue and at least one agent by use of at least one tissue equivalent, the apparatus comprising a container for the tissue equivalent, the container comprising:
  (i) means for positioning the tissue equivalent in the container, whereby the tissue equivalent defines at least one region in the container;
  (ii) at least one port; and
  (iii) means for closing the container; and
 (b) a tissue equivalent. In preferred embodiments, the tissue equivalent defines at least two regions.

In some embodiments of kits according to the present invention, the tissue equivalent defines an upper and a lower region in the container. In yet other embodiments wherein the tissue equivalent is a tubular tissue equivalent, the tubular tissue equivalent defines an inner and outer region in the container. In some such embodiments, the container is provided one or more liquid phases.

In preferred embodiments of kits according to the present invention, the apparatus is provided with two or more individual containers. In some such embodiments, the apparatus may be provided with means for hooking to a manifold in order to sample or perfuse individual containers. In yet other embodiments, the containers are interconnected so that the liquid phase adjacent to the tissue equivalents is common to all the tissue equivalent samples. In such kits, the tissue equivalent in each container is accessible for contact with the agent(s) and the liquid phase in each container is accessible for analysis.

Such kits further optionally comprise one or more agents as well as one or more of the reagents necessary for determining the interaction of the agent and the tissue equivalent. Various assay techniques known to those skilled in the art are used to determine the interaction of the tissue equivalent and the agent and, include, but are not limited to, histological analysis, mass spectrometry, magnetic resonance imaging, ultrasonic imaging, radioactive tracer methodologies, radioimmunoassay, enzyme immunoassay, enzyme-linked immunoassay, and fluorescent immunoassay.

The present invention provides also kits for determining the interaction of skin tissue with at least one agent. In one embodiment, such skin tissue equivalent based kits comprise in combination:
 (a) an apparatus for determining the interaction of skin tissue and at least one agent by use of at least one skin tissue equivalent, the apparatus comprising a container for the skin tissue equivalent, the container comprising:
- (i) means for positioning the skin tissue equivalent in the container, whereby the skin tissue equivalent defines an upper and a lower region in the container, the lower region further comprising a liquid phase; and
- (ii) at least one port; and
- (iii) means for closing the container; and
(b) a skin tissue equivalent having an epidermal and a dermal layer, the dermal layer being adjacent to the liquid phase.

In other embodiments, a second liquid phase is disposed between the skin tissue equivalent and the means for closing the container. In such embodiments, it may be desirable to remove the second liquid phase before contacting the agent and the skin tissue equivalent. In yet other embodiments the apparatus is provided with two or more individual containers or two or more interconnected containers.

Other embodiments of apparatus according to the present invention, e.g., embodiments comprising tubular tissue equivalents, such as tubular skin tissue equivalents, may be included in kits provided by the present invention.

In some embodiments of the present invention, it may be desirable to determine the interaction of an agent with different types of tissue. For example, the interaction of liver tissue and an agent which has penetrated the skin could be determined by first passing the agent through a skin tissue equivalent in accordance with the present invention, collecting the agent or its breakdown products, and then contacting the collected agent or breakdown products, with a liver tissue equivalent in accordance with the present invention.

Apparatus, methods and kits based on human blood vessel tissue equivalents are also provided by the present invention for use in determining the interaction of the blood vessel tissue equivalent and at least one agent. Such interactions include but are not limited to the effect(s) on vascular physiology, blood-surface interactions and pathological processes.

In general, a blood vessel tissue equivalent based test system comprises the appropriate type of blood vessel tissue equivalent incorporated into a circulatory loop. The circulatory loop is completely mechanical (pump, tubing, reservoir, etc.) or biological with the blood vessel tissue equivalent incorporated ex vivo as in an aterio-venous shunt. The circulating fluid is culture medium, culture medium containing blood elements such as platelets, heparinized blood, or (as in the ex vivo loop), untreated blood. Other cells such as macrophages are optionally added to the blood vessel tissue equivalent or the circulating fluid as desired.

FIGS. 4A and 4B show one embodiment of an apparatus in accordance with the present invention for determining the effect of one or more agents on blood vessels by use of blood vessel tissue equivalents, the apparatus comprising a container 10 for the blood vessel tissue equivalent, a cover means 70 for sealable connection thereto, the cover means 70 being provided with two ports 14, 16. The container 10 is further provided with two valved cannulae 15, 17 to provide means for positioning the blood vessel tissue equivalent in the container 10.

FIG. 4C is a schematic illustration of the container 10 shown in FIGS. 4A and 4B incorporated into a mock circulatory loop which comprises tubing 120, a reservoir 121, a pulsatile pump 122, the circulatory loop being provided with a port 123. The circulatory loop also comprises a pressure transducer (not shown) connected to an amplifier and chart recorder (not shown). The reservoir 121 is provided with a means (not shown) for bubbling gas through the circulating fluid to provide gas exchange.

The same general materials may be used for constructing the embodiment shown in FIGS. 4A and 4B as are described for use in constructing other embodiments described herein. As in other embodiments, the cover means for the container is optional, access to the container and tissue equivalent being provided via ports or other appropriate means.

Preferred materials for the tubing include medical grade tygon, teflon, silicon, stainless steel or other inert tubing.

Two examples of blood vessel equivalent based test systems are the atherogenesis test system and the metastasis bio-test System.

The atherogenesis test system is designed for the study of the formation and amelioration of atherosclerotic plaque in vitro. It consists of a mock circulatory loop, illustrated in FIG. 4C, comprising tubing 120, a blood vessel tissue equivalent 68 made with human arterial cells in a container 10, a pulsatile pump 122, a pressure transducer (now shown), and a fluid reservoir 121. The circulating fluid is hyperlipidemic serum or culture medium supplemented with known atherogenic factors such as low density lipoproteins. Macrophages are optionally included as precursors to foam cells. The blood vessel equivalent is subjected to local mechanical or other type of injury to induce plaque initiation (Ross & Glomset, 1976). The system allows the experimenter to manipulate the circulating fluid, the pressure and pressure changes, the constitutents of the artery equivalent, etc. to determine their role in atherogenesis and their response to pharmacological treatments.

The metastasis test system is designed for the study of the passage of cancerous cells across capillary walls. Most tumor metastases are blood-borne so the various steps in metastasis, including invasion of the vessel, circulation, attachment, and diapedesis are likely sites for general antitumor agents to act. A circulatory loop similar to that shown in FIG. 4C, is used. The metastasis bio-test system comprises a low pressure, low flow rate mock circulatory loop containing a capillary equivalent (either as a single tube lined with capillary endothelial cells or as a capillary network grown within a collagen lattice), and ports for adding transformed cells to either the luminal or abluminal fluid compartments of the blood vessel tissue equivalent. The time course and steps in the metastatic process, as well as their response to pharmacologic agents are easily studied in this in vitro system.

The present invention also includes kits for determining the interaction of blood vessel tisuse equivalents and at least one agent, similar to those kits described hereinabove.

The invention will be further understood with reference to the following examples, which are purely exemplary in nature, and are not meant to be utilized to limit the scope of the invention.

EXAMPLE 1—SKIN ABSORPTION TEST

Skin tissue equivalent(s) cast as a sheet used to test percutaneous absorption of benzoic acid (1) A dermal equivalent is cast with human dermal fibroblasts using the method of U.S. Pat. No. 4,485,096. A suitable size for casting is a total volume of 15 ml. in a Petri dish 100 mm in diameter.

(2) The dermal equivalent is seeded with human epidermal cells. Small droplets of a cell suspension, made with cultured epidermal cells or freshly dissociated epidermis, are applied to the surface of the dermal equivlent (See, e.g., U.S. Pat. No. 4,485,096). Alternatively, pieces (strips, punches, or other shapes) of skin or of skin tissue equivalent are applied to the surface of the dermal equivalent (See, e.g., U.S. Pat. No. 4,604,346). The seeded dermal equivalent is cultured to allow a complete epidermal layer to form.

(3) The lower half of the test chamber is filled with fluid (typically culture medium or buffered salt solution). The completed skin tissue equivalent is transferred to an apparatus in accordance with the present invention such as shown in FIGS. 1A or 1B, chamber so that the entire lower chamber and gasket are covered. The upper gasket is placed on upper surface of the skin tissue equivalent. The diameter of the chamber is about 25 mm. The upper half of the test chamber is screwed on tightly enough to make an effective seal without crushing the skin tissue equivalent.

(4) Any excess fluid is aspirated from the upper surface of the skin tissue equivalent. Flow of buffered salt solution or other collection fluid is started through the lower chamber and collected in a fraction collector.

(4) The agent(s) may be applied, its passage through skin tissue equivalent assayed, and time course and absorption calculated as in *J. Pharm. Sci.* 74, 65–67 (1985). The test sample is applied to the upper surface of the skin tissue equivalent. For example, [$^{14}$C] Benzoic acid in petrolatum as a vehicle (suitable concentrations are 10, 100, and 1,000 ng/mg) with 25 mg of vehicle applied per cm$^2$ of skin tissue equivalent.

(6) Samples of the effluent are collected and counted by standard methods known in the art in a liquid scintillation counter. Alternatively, the skin tissue equivalent sample itself may be washed (with buffered saline), removed from the container, solubilized (for example in a solution 0.5% sodium dodecyl sulfate and 4 M urea in water), and aliquots counted to determine radioactivity trapped in the skin tissue equivalent. This approach is useful for hydrophobic compounds which may not readily pass from the skin tissue equivalent into the collection fluid.

This method is further refined by separating the epidermal and dermal layers using methods known to those skilled in the art, e.g., mild trypsin treatment.

EXAMPLE 2—SKIN CELL PERMEABILITY TEST (1) Prepare and mount the desired amount of skin tissue equivalents in apparatus in accordance with the present invention as described in example 1, above.

(2) Apply the agent(s) to upper (epidermal) surface of the skin tissue equivalent A. As an example the chemicals used in the FRAME test (Bells, M. & Bridges, J. W., in *Acute Toxicity Testing; Alternative Approaches*, pp. 63–79, 1984; A. M. Goldberg, ed., M. A. Liebert, Inc., New York), are applied to individual samples of skin tissue equivalent in aqueous solutions at various concentrations.

(3) The effluent fluid is collected from the lower chamber and assayed for a cytoplasmic enzyme produced by the skin tissue equivalent in response to the agent(s) (e.g., Lactate Dehydrogenase, EC 1.1.1.27) and a lysosomal enzyme (e.g., β-glucuronidase, EE 3.2.1.31). The enzyme released is assayed by standard methods known to those skilled in the art (See, e.g., *Methods of Enzymatic Analysis*. H. U. Bergmeyer, E. Verlag Chemie, Weinheim, 1983 III, 118–138 and IV, 246–256 respectively).

(4) Dose response curves of enzyme release which is related to cellular damage are prepared from the data.

EXAMPLE 3—SKIN IMMUNOREACTIVITY TEST (1) A container is used which consists of two chambers defined by a membrane or mesh. See, e.g., FIG. 1B. The membrane or mesh is a disk about 25 mm in diameter and has an average pore size in the range 0.5 to 3.0 μm. The membrane is made of, or coated with, a material to which cells and collagen adhere (e.g., glow discharge treated polystyrene or collagen coated controlled pore size glass). The lower chamber is provided with ports for medium sampling or flow-through. The upper chamber is provided with a cover means, removable for sample application. The walls of the upper chamber do not promote cell adhesion (e.g., polycarbonate, TEFLON ®, or siliconized polystyrene).

(2) A dermal equivalent is cast, as described in Example 1, above, in the upper chamber. In addition to dermal fibroblasts, the mixture contains cells of the immune system. One or more of the following cell types are included: Langerhans cells, macrophages, T-cells, mast cells and microvascular endothelial cells. Other cell types may be included as desired. A specific formulation includes Langerhans cells, macrophages, and mast cells.

(3) The dermal equivalent contracts, constrained by adhesion to the membrane, to form a disk which separates the upper and lower chambers.

(4) The dermal equivalent is seeded with epidermal cells (typically 3–10 days after casting). The skin tissue equivalent is cultured to develop a fully keratinized epidermal layer. See, e.g., *J. Invest. Dermatology* 81:25–105 (1983);

(5) An agent (potential allergen) is applied to the epidermal surface. One or more mediators of allergic responses is collected in the lower chamber and assayed by standard means. Examples include interleukin-1 (IL-1) released by Langerhans cells and macrophages, and histamine released by mast cells.

EXAMPLE 4—SKIN CHEMICAL RESPONSE TEST

Irritant Chemical (1) The mandrel 100 and container 10 shown in FIGS. 2 and 3 are assembled. A dermal equivalent is cast through port 72 as described in Example 1 in the volume or space defined by the mandrel 100 and the container 10 as assembled. The volume of dermal equivalent casting mixture is adjusted so that the entire mesh 104 and means for cells to adhere 103 are covered. Thus, for the dimensions given, a volume of about 50–60 ml would be required. The dermal equivalent is allowed to gel and to contract around the mandrel 100.

The holes 103, 107, limit longitudinal contraction so that the mesh or membrane portion 104 remains completely covered. If necessary, the lumen of the mandrel 100 can be filled through port 71 simultaneously with the container 10 to prevent flow of the casting mixture into the lumen of the mandrel 100.

(2) Then (typically after 3-10 days), the dermal equivalent will be seeded with a suspension of epidermal cells through the port 72. A multiple barrelled micropipettor is inserted through port 72 and tiny droplets (typically 1.5 μl) of a cell suspension are applied so that the entire surface of the dermal equivalent is uniformly seeded with epidermal cells. These are grown to form a keratinized epidermal layer.

(3) The agent(s) is then applied to the epidermal layer of the formed skin tissue equivalent and the lumen of the mandrel is perfused with the collection fluid. An irritant substance (See, e.g., M. Steinberg et al. (*In Animal Models in Dermatology.* H. Maibach, ed., Churchill Livingstone, 1975, pp. 1-11)) may be applied in a dressing (e.g., gauze pad). This is occluded by covering with an impermeable material, e.g., plastic film, if desired. The test dressing is removed after a suitable time (e.g., 24 hr).

(4) The perfusate is assayed for substances released by the cells in response to the agent(s) (e.g., Prostaglandin $E_2$) using methods known to those skilled in the art. For example, commercially available Prostaglandin $E_2$ radioimmunoassay kits may be used.

EXAMPLE 5—INCORPORATION OF BLOOD VESSEL TISSUE EQUIVALENT INTO MOCK CIRCULATORY LOOP

1. A blood vessel tissue equivalent was made using arterial cells as described in *Science.* 231: 397-400 (1986). The blood vessel tissue equivalent was fabricated with an inside diameter of about 6 mm and a length of about 10 cm.

(2) It was transferred to a container 10 (See, e.g., FIGS. 4A, 4B) and tied onto the end of the cannulae disposed inside the container 10 by means of 4-0 silk ligatures. The ligatures were tightened sufficiently to hold the blood vessel tissue equivalent firmly without cutting through the blood vessel equivalent wall.

(3) The container was incorporated into a mock circulatory loop as shown in FIG. 4C.

(4) Culture medium was circulated through the loop. The blood vessel equivalent dilated and contracted with changes in pressure. Pressure variations were achieved within physiological pressure ranges (80-200 mm Hg) and frequencies (60-100 pulsations per minute).

EXAMPLE 6—ATHEROGENESIS TEST (1) Several blood vessel tissue equivalent(s) are transferred into apparatus provided by the present invention as described in Example 5 and the apparatus are incorporated into mock circulatory loops as illustrated in FIG. 4C.

(2) In all but the control blood vessel tissue equivalents, the circulatory medium is supplemented with atherogenic factors such as low density lipoprotein (LDL), which is a major cholesterol carrier in the bloodstream.

(3) Local injuries are produced by mechanical, thermal, or other means in the endothelial lining of the blood vessel tissue equivalents.

(4) The blood vessel tissue equivalents are subjected to high pulsatile pressures (e.g., peak about 200 mm Hg; valley about 120 mm Hg).

(5) The blood vessel tissue equivalents are examined at various times for indications of artherogenesis, e.g., for proliferative lesions (atherosclerotic plaques) in the wall and for deposits of lipid (principally cholesterol) at the sites of local injury.

Standard histological techniques are used for the examination. Non-invasive techniques could be developed which include ultrasound or Magnetic Resonance Imaging (MRI).

EXAMPLE 7—METASTASIS TEST

Used to Determine if Metastatic Potential is Correlated With Ability to Cross Blood Vessel Tissue Equivalent Wall (1) Blood vessel tissue equivalents are prepared as described in Example 5 except that capillary endothelial cells are used rather than arterial endothelial cells. The blood vessel tissue equivalents are incorporated into mock circulatory loops illustrated in FIG. 4C. A simple peristaltic pump provides sufficient perfusion.

(2) In all but control blood vessel tissue equivalents, transformed cells (e.g., B12 melanoma cells) are injected into the circulatory loop. The fluid in the abluminal compartment of the perfusion chamber is collected and replaced at intervals.

(3) The cells which cross the blood vessel tissue equivalent wall into the inner region are collected by centrifugation, counted and injected into mice. The metastatic potential is determined according to Poste & Fidler, *Nature.* 283:139-146 (1981) and correllated with the time that the sample is collected. Alternatively, the blood vessel tissue equivalent could be perfused with clones of differing metastatic potential and the rate at which the cells from different clones cross the blood vessel tissue equivalent wall could be measured.

It is understood that the examples and embodiments described herein are for illustrative purposes only, and that various modifications or changes in light thereof that will be suggested to persons skilled in the art are to be included in the spirit and purview of this application and the scope of the approved claims.

We claim:

1. A method of determining the interaction of tissue and at least one agent by use of at least one tissue equivalent, the method comprising the steps of:
    a. contacting the agent with a tissue equivalent, wherein the tissue equivalent is adjacent to a liquid phase; and
    b. determining the interaction of the tissue equivalent and the agent by analyzing at least one of (i) the tissue equivalent, (ii) an intracellular fluid of the tissue equivalent, or (iii) the liquid phase.

2. The method of claim 1 wherein the tissue equivalent is skin tissue equivalent having an epidermal and dermal layer, the dermal layer of the skin tissue equivalent being adjacent to the liquid phase.

3. The method of claim 1, wherein the interaction of the tissue equivalent and the agent comprises the passage of the agent into or through the tissue equivalent, and the interaction is determined by measuring at least one of (i) the tissue equivalent, (ii) an intracellular tissue fluid of the tissue equivalent, or (iii) the liquid phase to detect the presence of the agent.

4. The method of claim 1, wherein the interaction of the tissue equivalent and the agent comprises the production or release of one or more substances by the tissue equivalent, and the interaction is determined by measuring at least one of (i) the tissue equivalent, (ii) an intracellular fluid of the tissue equivalent, or (iii) the liquid phase to detect the presence or absence of the substance.

5. The method of claim 1, wherein the interaction of the tissue and the agent comprises a change in (i) permeability, (ii) proliferation, (iii) differentiation, or (iv) configuration, of cells of the tissue equivalent.

6. The method of claim 1 wherein the interaction of the tissue and the agent protects the tissue.

7. The method of claim 1, wherein the tissue equivalent is a tubular tissue equivalent.

8. The method claim 7, wherein the tubular tissue equivalent is a skin tissue equivalent or a blood vessel tissue equivalent.

9. A method of determining the interaction of skin tissue and at least one agent by use of at least one skin tissue equivalent, the skin tissue equivalent having an epidermal and a dermal layer, the method comprising the steps of:
  a. contacting the agent with the epidermal layer of the skin tissue equivalent, wherein the dermal layer of the skin tissue equivalent is adjacent to a liquid phase; and
  b. determining the interaction of the skin tissue equivalent and the agent by analyzing at least one of (i) the skin tissue equivalent, (ii) an intracellular fluid of the skin tissue equivalent, or (iii) the liquid phase.

10. The method of claim 9, wherein the interaction comprises passage of the agent into or through the skin tissue equivalent or the production or release of one of more substances by the skin tissue equivalent, and the interaction is determined by analyzing at least one of (i) the skin tissue equivalent, (ii) an intracellular fluid of the skin tissue equivalent, or (iii) the liquid phase, to detect the presence or absence of the agent or the substance.

11. A method of determining the interaction of tissue and at least one agent by use of at least one tubular tissue equivalent, the method comprising:
  a. contacting the agent with the lumen or the abluminal surface of the tubular tissue equivalent, contact being effected by providing a liquid phase adjacent to the lumen or the abluminal surface of the tubular tissue equivalent and introducing the agent into the liquid phase; and
  b. determining the interaction of the tubular tissue equivalent and the agent by analyzing at least one of (i) the tubular tissue equivalent, (ii) the intracellular fluid of the tubular tissue equivalent, or (iii) the liquid phase.

12. A method of determining the interaction of tissue and at least one agent by use of at least one tubular tissue equivalent, the method comprising:
  a. contacting the agent with the tubular tissue equivalent, wherein (i) the lumen of the tubular tissue equivalent is adjacent to a first liquid phase, and (ii) the abluminal surface of the tubular tissue equivalent is adjacent to a second liquid phase, contact being effected by introducing at least one agent to the first or second liquid phase; and
  b. determining the interaction of the tubular tissue equivalent and the agent by analyzing at least one of (i) the tubular tissue equivalent, (ii) an intracellular fluid of the tubular tissue equivalent, (iii) the first liquid phase, or (iv) the second liquid phase.

13. The method of claim 11, wherein the tubular tissue equivalent is skin tissue equivalent or blood vessel tissue equivalent.

14. An apparatus for determining the interaction of tissue and at least one agent by use of at least one tissue equivalent, the apparatus comprising the tissue equivalent and a container for the tissue equivalent, the container comprising:
  (i) means for positioning the tissue equivalent in the container, whereby the tissue equivalent defines at least one region in the container;
  (ii) at least one port; and
  (iii) means for closing the container.

15. An apparatus for determining the interaction of tissue and at least one agent by use of at least one tissue equivalent, the apparatus comprising the tissue equivalent and a container for the tissue equivalent, the container comprising:
  (i) means for positioning the tissue equivalent in the container, whereby the tissue equivalent defines at least two regions in the container;
  (ii) at least one port; and
  (iii) means for closing the container.

16. An apparatus according to claim 15, wherein the means for closing the container comprises a cover means, removably sealable to the container.

17. An apparatus according to claim 15, wherein the means for closing the container comprises an opening or a port, the opening or port having a valve or cover means.

18. An apparatus according to claim 15 further comprising at least two containers.

19. An apparatus according to claim 18 wherein the containers are interconnected.

20. An apparatus according to claim 15, wherein the tissue equivalent defines an upper and a lower region in the container.

21. An apparatus according to claim 20, wherein the lower region further comprises a liquid phase and one surface of the tissue equivalent is adjacent to the liquid phase.

22. An apparatus according to claim 15, wherein the tissue equivalent is skin tissue equivalent having an epidermal and a dermal layer, the dermal layer being adjacent to the liquid phase.

23. An apparatus according to claim 21, wherein the upper region further comprises a second liquid phase and one surface of the tissue equivalent is adjacent to the second liquid phase.

24. An apparatus according to claim 15, wherein the container is provided with at least two ports.

25. An apparatus in accordance with claim 15, wherein the means for positioning the tissue equivalent in the container is disposed in the container and comprises a permeable member.

26. An apparatus in accordance with claim 25, wherein the tissue equivalent is cast on the permeable member.

27. An apparatus in accordance with claim 25, wherein the permeable member comprises a selectively permeable membrane or mesh.

28. An apparatus according to claim 15, wherein the tissue equivalent is a tubular tissue equivalent and defines an inner and outer region in the container, the inner region comprising a first liquid phase and the outer region comprising a second liquid phase.

29. An apparatus according to claim 28, further comprising at least two containers.

30. An apparatus according to claim 29, wherein the containers are interconnected.

31. An apparatus according to claim 28, wherein the means for positioning the tubular tissue equivalent in the container comprises valved cannulae, portions of which are disposed inside the container.

32. An apparatus according to claim 28, wherein the means for positioning the tubular tissue equivalent in the container comprises (i) means for attaching the tubular tissue equivalent.
    (ii) means for limiting the longitudinal contraction of the tubular tissue equivalent, and (iii) means for allowing selected materials to pass between the tubular tissue equivalent and at least one of the first or second liquid phases.

33. An apparatus according to claim 32 wherein the means for attaching the tubular tissue equivalent to the means for positioning comprises a textured, inert material.

34. An apparatus according to claim 33, wherein the textured inert material is VELCRO ® textured stainless steel, textured TEFLON ®, or a textured plastic.

35. An apparatus according to claim 34, wherein the textured plastic is polycarbonate, polystyrene or polyurethane foam.

36. An apparatus according to claim 28, wherein the tubular tissue equivalent is provided with at least one support member.

37. An apparatus according to claim 32, wherein the tubular tissue equivalent is cast around the means for positioning the tubular tissue equivalent in the container.

38. An apparatus according to claim 28, wherein the apparatus is incorporated into a circulatory loop.

39. A method of determining the interaction of tissue and at least one agent with the aid of the apparatus of claim 15, the method comprising the steps of:
    a. contacting the agent with the tissue equivalent; and
    b. determining the interaction of the tissue equivalent and the agent by analyzing at least one of (i) the tissue equivalent, (ii) an intracellular fluid of the tissue equivalent, or (iii) the liquid phase.

40. The method of claim 39, wherein the apparatus is further provided with means for changing, sampling, circulating or feeding the liquid phase.

41. The method of claim 40, wherein the liquid phase is sampled and analyzed on a periodic or a continuous basis.

42. A method of determining the interaction of tissue and at least one agent with the aid of the apparatus of claim 28, the method comprising the steps of:
    a. contacting the agent with the tubular tissue equivalent; and
    b. determining the effect of the agent on the tubular tissue equivalent by analyzing at least one of (i) the tissue equivalent, (ii) an intracellular fluid of the tissue equivalent, (iii) the first liquid phase, or (iv) the second liquid phase.

43. The method of claim 42, wherein the apparatus is further provided with means for moving at least one of the liquid phases at a predetermined rate or frequency.

44. The method of claim 43, wherein at least one of the liquid phases is sampled and analyzed on a periodic or continuous basis.

45. The method of claim 43, wherein the second liquid phase is circulated through the tubular tissue equivalent to simulate the flow of blood.

46. A kit comprising, in combination:
    (a) an apparatus in accordance with claim 15; and
    (b) a tissue equivalent.

47. A kit according to claim 46, further comprising a tissue equivalent wherein the tissue equivalent defines an upper and a lower region in the container, the lower region further comprising a liquid phase, wherein one surface of the tissue equivalent is adjacent to the liquid phase.

48. A kit according to claim 47, wherein the upper region further comprises a second liquid phase, wherein a surface of te tissue equivalent is adjacent to the second liquid phase.

49. A kit according to claim 46, wherein the apparatus is provided with two or more individual containers.

50. A kit according to claim 49, wherein the containers are interconnected so that the liquid phase is common to each container.

51. A kit according to claim 46, wherein the container is provided with at least two ports.

52. A kit according to claim 48, wherein the tissue equivalent is skin tissue equivalent having an epidermal and a dermal layer, the epidermal layer being adjacent to the second liquid phase, and the dermal layer being adjacent the first liquid phase.

53. A kit according to claim 46, further comprising a tubular tissue equivalent, wherein the tubular tissue equivalent defines an inner and outer region in the container, the inner region comprising a first liquid phase and the outer region comprising a second liquid phase.

54. A kit according to claim 53, wherein the tubular tissue equivalent is a skin tissue equivalent or a blood vessel tissue equivalent.

* * * * *